United States Patent
Faram

(10) Patent No.: US 7,191,780 B2
(45) Date of Patent: Mar. 20, 2007

(54) CONTINUOUS HIGH-FREQUENCY OSCILLATION BREATHING TREATMENT APPARATUS

(75) Inventor: Joseph Dee Faram, Dallas, TX (US)

(73) Assignee: Comedica Incorporated, Dallas, TX (US)

( * ) Notice: Subject to any disclaimer, the term of this patent is extended or adjusted under 35 U.S.C. 154(b) by 625 days.

(21) Appl. No.: 10/666,428

(22) Filed: Sep. 22, 2003

(65) Prior Publication Data

US 2005/0061318 A1    Mar. 24, 2005

(51) Int. Cl.
*A61M 11/00* (2006.01)
*A61M 15/00* (2006.01)
*A61M 16/00* (2006.01)

(52) U.S. Cl. .......................... 128/204.25; 128/200.14; 128/200.16; 128/200.18; 128/200.21; 128/203.14; 128/204.14; 128/204.24

(58) Field of Classification Search ........... 128/200.14, 128/200.16, 200.18, 200.21, 203.14, 204.14, 128/204.24
See application file for complete search history.

(56) References Cited

U.S. PATENT DOCUMENTS

| | | | | |
|---|---|---|---|---|
| 3,068,856 A * | 12/1962 | Bird et al. | ............. | 128/203.12 |
| 3,584,621 A * | 6/1971 | Bird et al. | ............. | 128/200.18 |
| 3,630,196 A * | 12/1971 | Bird et al. | ............. | 128/200.18 |
| 3,664,337 A * | 5/1972 | Lindsey et al. | ........ | 128/200.18 |
| 4,195,044 A * | 3/1980 | Miller | ........................ | 261/142 |
| 4,263,907 A * | 4/1981 | Lindsey | ................. | 128/200.18 |
| 4,471,773 A * | 9/1984 | Bunnell et al. | ........ | 128/204.21 |
| 4,592,349 A * | 6/1986 | Bird | ...................... | 128/204.25 |
| 4,747,402 A * | 5/1988 | Reese et al. | ............ | 128/204.21 |
| 4,805,613 A * | 2/1989 | Bird | ...................... | 128/204.25 |
| 4,823,784 A * | 4/1989 | Bordoni et al. | ........ | 128/200.14 |
| 4,838,260 A | 6/1989 | Bird | | |
| 4,930,501 A | 6/1990 | Bird | | |
| 5,007,420 A * | 4/1991 | Bird | ...................... | 128/200.14 |
| 5,116,088 A | 5/1992 | Bird | | |
| 5,165,398 A | 11/1992 | Bird | | |
| 5,277,175 A * | 1/1994 | Riggs et al. | ........... | 128/200.21 |
| 5,415,161 A * | 5/1995 | Ryder | .................... | 128/200.23 |
| 5,479,920 A * | 1/1996 | Piper et al. | ............ | 128/204.23 |
| 5,570,682 A * | 11/1996 | Johnson | ................. | 128/200.14 |
| 5,617,844 A * | 4/1997 | King | ..................... | 128/200.18 |
| 5,694,919 A * | 12/1997 | Rubsamen et al. | .... | 128/200.14 |
| 5,862,802 A * | 1/1999 | Bird | ...................... | 128/204.18 |
| 6,269,810 B1 * | 8/2001 | Brooker et al. | ....... | 128/203.12 |
| 6,435,175 B1 * | 8/2002 | Stenzler | ................ | 128/200.14 |
| 6,581,596 B1 * | 6/2003 | Truitt et al. | ........... | 128/204.21 |
| 6,595,203 B1 * | 7/2003 | Bird | ...................... | 128/200.21 |
| 6,729,327 B2 * | 5/2004 | McFarland, Jr. | ....... | 128/203.12 |
| 6,805,118 B2 * | 10/2004 | Brooker et al. | ....... | 128/203.12 |
| 6,880,556 B2 * | 4/2005 | Uchiyama et al. | ..... | 128/205.24 |
| 7,013,894 B2 * | 3/2006 | McFarland, Jr. | ....... | 128/205.24 |
| 7,077,133 B2 * | 7/2006 | Yagi et al. | ............. | 128/204.26 |
| 7,131,439 B2 * | 11/2006 | Blacker et al. | ........ | 128/200.18 |
| 2003/0140921 A1 * | 7/2003 | Smith et al. | ........... | 128/200.14 |

(Continued)

*Primary Examiner*—Teena Mitchell
*Assistant Examiner*—Adam Brandt
(74) *Attorney, Agent, or Firm*—Hitchcock Evert LLP

(57) ABSTRACT

A continuous high-frequency oscillation breathing device delivers therapy during both inhalation and exhalation in order to assist in clearings secretions the lungs. A fixed shrouded-venturi patient interface circuit is combined with medicated aerosol to deliver continuous high-frequency oscillation therapy. Fixed open apertures in the patient interface circuit allow ingress and egress of flow, and are calibrated to allow exhalation and prevent stacking of successive breaths.

48 Claims, 7 Drawing Sheets

U.S. PATENT DOCUMENTS

2003/0145849 A1* 8/2003 Drinan et al. .......... 128/200.14
2003/0183226 A1* 10/2003 Brand et al. ........... 128/200.23
2005/0150489 A1* 7/2005 Dunfield et al. ....... 128/200.14
2005/0172954 A1* 8/2005 Smith et al. ........... 128/200.14
2005/0217666 A1* 10/2005 Fink et al. ............. 128/200.14

* cited by examiner

CONTINUOUS HIGH-FREQUENCY OSCILLATION BREATHING TREATMENT APPARATUS

FIELD OF THE INVENTION

The invention relates to a therapeutic breathing device which delivers continuous high-frequency oscillation therapy during both inhalation and exhalation to facilitate the removal of mucus secretions from the lungs.

BACKGROUND OF THE INVENTION

Healthy people are able to clear mucus secretions from their lungs by means of bi-directional airflow and a system of tiny hairlike follicles called "mucociliary escalators." Airflow passing over the secretions creates shear forces that combine with the mucociliary escalators to transport mucus from the lower respiratory tract to upper airways. From there the secretions can be removed by coughing.

However, during illness a person's normal ability to remove secretions may become impaired. As the natural secretion clearance mechanism becomes more challenged, secretions may build up in the lungs, bronchial and tracheal passages creating a heightened potential for further exacerbation of illness. Retained mucus secretions in the warm, moist environment of the lungs create an excellent opportunity for the growth of bacteria. In addition, retained secretions may hinder the lungs' ability to exchange gas and increase the risk of pulmonary neoplasm. Keeping the lungs open and clear of secretions is integral to maintaining a healthy defense of the pulmonary system.

As the population ages, and the quality of air decreases, assaults on the respiratory system continue to rise. In addition to curable pulmonary infections, there are some 16 million people in the United States alone diagnosed with chronic lung disease, and it is estimated that an additional 16 million cases go undiagnosed. Associated costs in both healthcare and lost production hours are staggering.

Because of the rising costs associated with pulmonary disease and the importance of keeping the lungs clear, clinicians and patients alike seek simple, inexpensive therapy devices that can enhance secretion mobilization. However, despite the variety of devices available, few show evidence of overall benefit.

In the late 1970's a Swedish anesthesiologist pioneered the use of "high frequency ventilation" for life support by programming a ventilator to deliver 60 breaths per minute, or 1 hertz. Subsequently the application of high-frequency delivery of gas to the airways was found to show favorable results in mobilizing secretions, especially when combined with medicated aerosol. While exact mechanisms of this therapy are not fully understood, it is likely that, as the column of air in the airways is oscillated by the high-frequency pulses of gas, the viscosity of the mucus is reduced by the untangling of some of the larger molecule strands, such as DNA and F-actin, which tend to be present as a byproduct of infection. Additionally, the high-frequency, intermittent delivery of gas contributes to a bi-directional flow creating wind shear forces which, in turn, help to mobilize the secretions in a cephalad fashion. However, in spite of therapeutic promise, the vast majority of those in need of this therapy do not have access to it because current technology is too complex and, therefore, ultimately too expensive.

U.S. Pat. Nos. 4,592,349, 4,805,613, 4,838,260, 4,930,501, 5,007,420, 5,116,088, 5,165,398, and 5,862,802 describe ventilators that combine high-frequency oscillation gas flow with aerosol. However, because these ventilators are designed primarily for life support, they connect to the patient via patient adapters that incorporate relatively complex mechanized valves that open and close between phasic shifts from inhalation to exhalation.

U.S. Pat. No. 4,592,349 describes a "pneumatic clutching means" as an exhalation valve assembly with a venturi slidably mounted within in such a way as to move between open and closed positions. Although highly effective in delivering life-support ventilation, the sliding venturi patient adapter is too complex, bulky, and costly to manufacture to be included in a simple, inexpensive therapy device. The patient interface necessitates the fabrication of a number of moving parts made of a variety of materials. The resulting friction of the constant sliding between open and closed positions eventually fatigues valve components that must be replaced. Additionally, the sliding venturi patient interface requires critical dimensions that prevent a reduction in its size and weight.

Although an alternate embodiment of a patient adaptor to be used with the above devices described in U.S. Pat. No. 4,592,349 utilizes a fixed venturi, it, nonetheless, must incorporate or attach to a mechanical exhalation valve that opens and closes between inhalation and exhalation. This design, again, although effective in delivering life-support ventilation, renders the patient connector too complex and costly to be used in a simple, inexpensive breathing therapy device.

In addition to being expensive because of their complexity of manufacturing and maintenance, the devices currently capable of delivering high-frequency oscillatory therapy to the lungs are complicated and difficult to use. They require either significant training of the patient or a trained professional to administer the therapy. U.S. Pat. No. 4,592,349, cited above, also describes a simpler version of these life-support ventilators which is specifically intended for therapeutic use. However, even this simpler, scaled-down version is designed with a mechanism to terminate the delivery of gas during exhalation, as well as adjustments for both pressure and pulse frequency during a therapy session. This design renders the device both costly to manufacture and complex to use.

SUMMARY OF THE INVENTION

The present invention is a simple apparatus for delivering continuous high-frequency oscillation therapy to the lungs during both inhalation and exhalation in order to assist in mucus secretion clearance. It comprises a pressurized gas source, a pressure reduction regulator, a flow interrupter, a nebulizer, and a fixed, open-aperture, shrouded venturi within the patient interface.

Accordingly, an object of the present invention is to provide a continuous high-frequency oscillation breathing treatment device that can be manufactured simply and inexpensively.

Another object of the invention is to provide a continuous high-frequency oscillation breathing treatment device that is sufficiently simple to use so that it requires little or no training.

Another object of the present invention is to provide a continuous high-frequency oscillation breathing treatment device that delivers pulses to the patient and allows the patient to exhale into it without stacking successive volumes of gas in the airways.

Another object of the invention is to provide a continuous high-frequency oscillation breathing treatment device that will be simple and inexpensive to maintain.

Another object of the invention is to provide a continuous high-frequency oscillation breathing treatment device that maximizes safety during use.

Another object of the invention is to provide a continuous high-frequency oscillation breathing treatment device that is sufficiently small and lightweight enough to be conveniently transported.

BRIEF DESCRIPTIONS OF THE DRAWINGS

REFERENCE NUMERALS IN DRAWINGS

1 Source Gas
2 Source Gas Supply Tube
3 Pressure Reduction Regulator
4 Tube
5 Connector Tee
6 Tube
7 Flow Interrupter
8 Tube
9 Circuit Connector
10 Circuit Tube
11 Breathing Head Assembly
12 Circumferential Communication Space
13 Injector Nozzle
14 Aft Apertures
15 Forward Apertures
16 Rear Flange Communication Ports
17 Venturi Tube
18 Mouthpiece
19 Mouthpiece Opening
20 Aerosol Entrainment Port
21 Nebulizer
22 Tube
23 Reducing Orifice
24 Circuit Connector
25 Circuit Tube
26 Forward Flange Communications Ports
27 Forward Flange Communications Ports
28 Forward Venturi Support Flange
29 Forward Venturi Support Flange
30 Rear Venturi Support Flange
31 Aperture Adjustment Collar
32 Aperture Adjustment Collar Holes
33 Safety Crowns
34 Timer
35 Patient Compliance Monitor
36 Reservoir Tee
37 Tube
38 Medicament Reservoir
39 Tube
40 Specified Gas Source
41 Inspiratory Gas Connector
42 RFID Transceiver
43 RFID Tag
44 Ventilator Circuit Inspiratory Limb
45 Ventilator Circuit Expiratory Limb
46 Ventilator Circuit Y
47 Ventilator Circuit Y Patient Connector
48 Evacuation Reservoir Tube
49 Evacuation Reservoir

DESCRIPTION OF A PREFERRED EMBODIMENT

Figure 1:
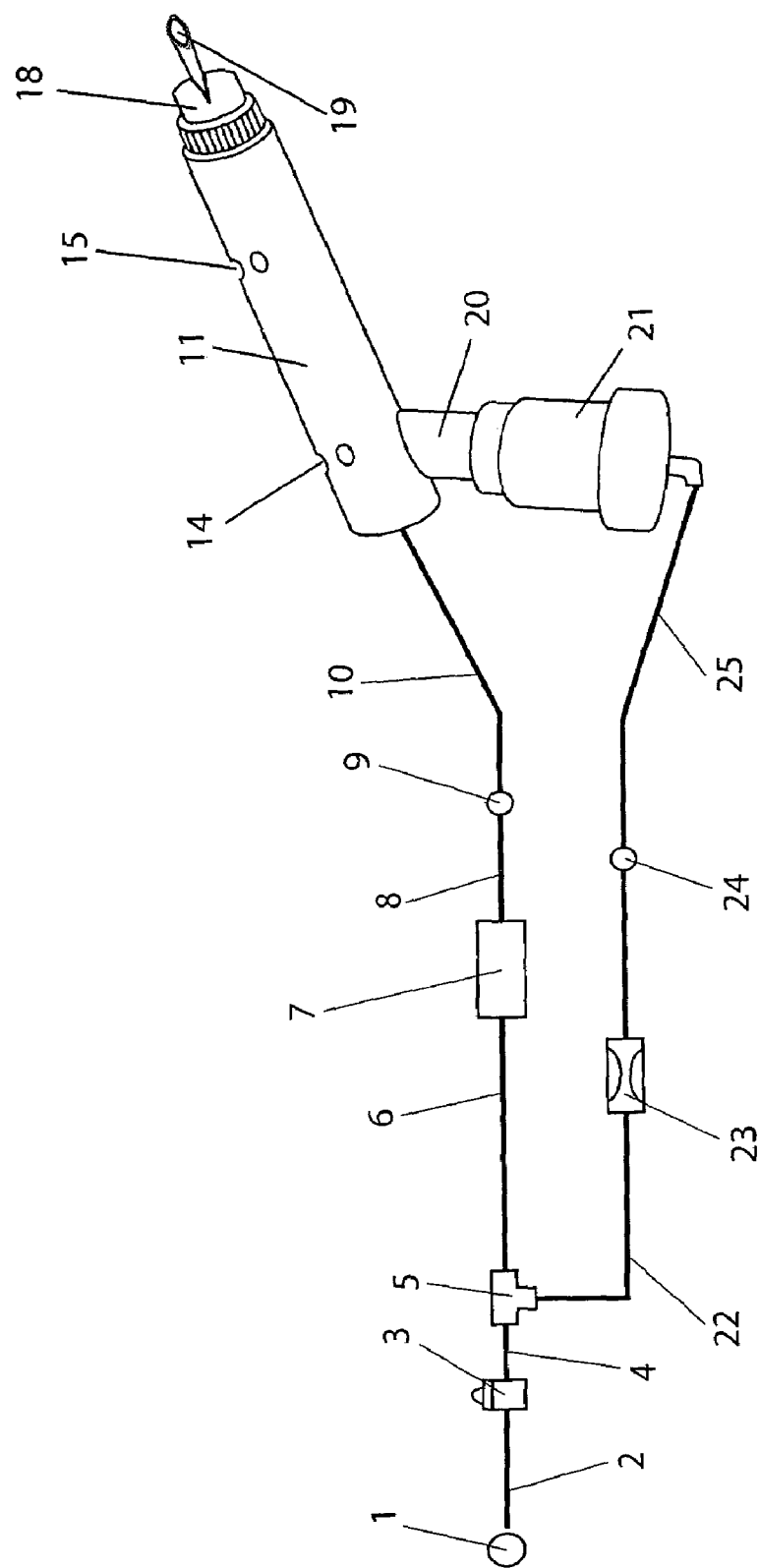
FIG. 1 is a schematic representation of the continuous high-frequency oscillation breathing therapy apparatus of present invention.

FIG. 1 shows a schematic diagram of a continuous high-frequency oscillation breathing treatment apparatus comprising a source of pressurized gas attached to a source gas 1, a gas supply tube 2, a reduction regulator 3, a flow interrupter valve 7, and a patient interface circuit comprised of circuit tubes 10 and 25, a breathing head assembly 11 and a nebulizer 21. Source gas 1 connects to pressure reduction regulator 3 by means of a source gas supply tube 2. Pressure reduction regulator 3 is connected via small a bore (⅛" ID) tube 4 to connector tee 5. One end of connector tee 5 attaches to tube 22 and the other end of connector tee 5 attaches to tube 6.

A tube 22, which has within it a reducing orifice 23, connects by one end to connector tee 5 and by the other end to circuit connector 24. Circuit tube 25 connects by one end to circuit connector 24 and by the other end to nebulizer 21.

Tube 6 connects by one end to connector tee 5 and by the other end to flow interrupter valve 7, for example, a pneumatic "logic cell cartridge", model A50146, manufactured by Percussionaire Corp. The other end of flow interrupter valve 7 is connected to tube 8 which connects to circuit connector 9. Circuit connector 9 connects to one end of circuit tube 10, and the other end of circuit tube 10 connects to the rearmost end of breathing head assembly 11.

Located on top toward the rear of breathing head assembly 11 are aft apertures 14. Forward apertures 15 are positioned approximately three-fourths of the way toward the front of breathing head assembly 11. Mouthpiece 18 and mouthpiece opening 19 are at the front end of breathing head assembly 11. Nebulizer 21 is connected to aerosol entrainment port 20 located on the bottom toward the rear end of breathing head assembly 11.

Figure 2:
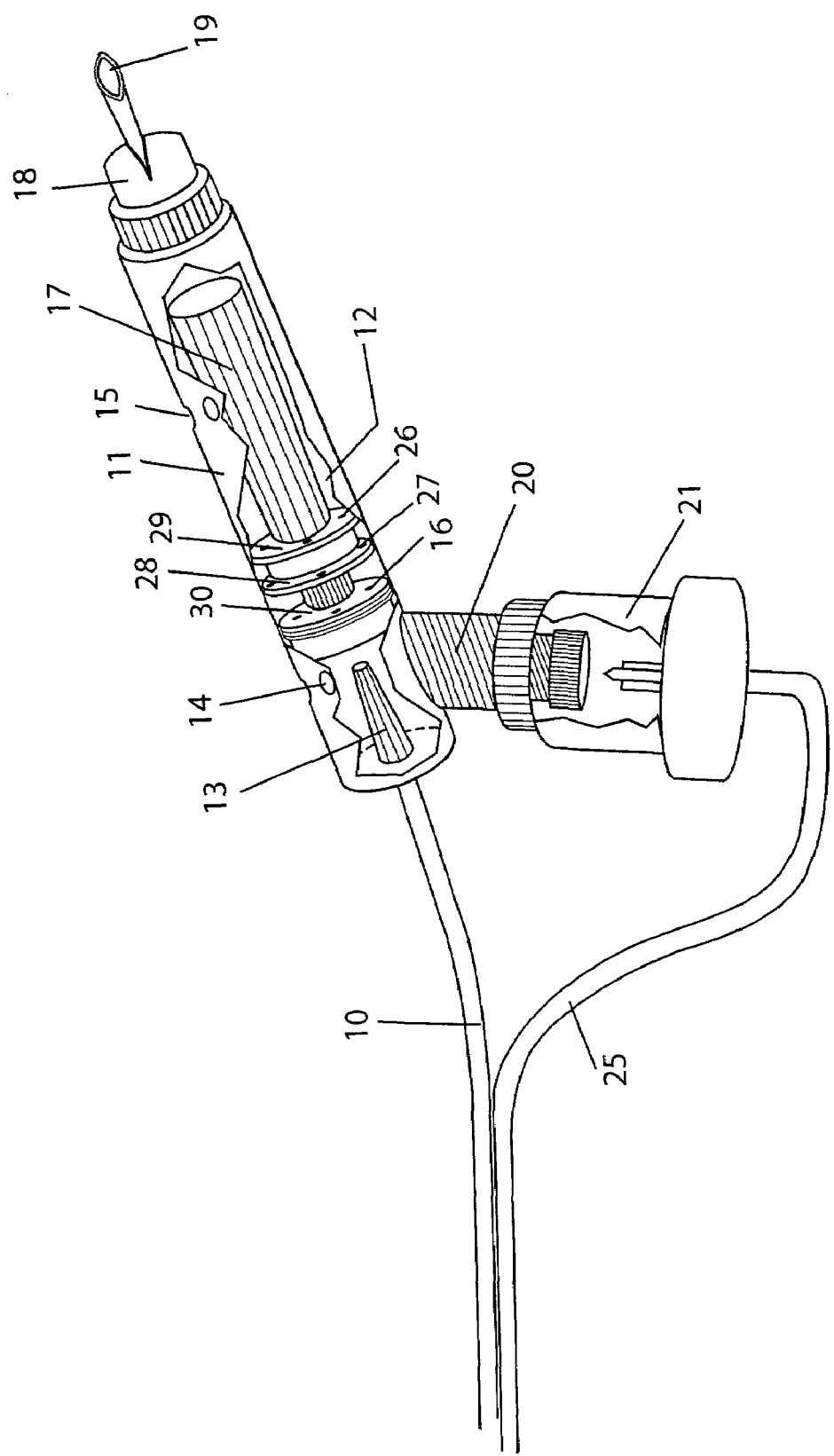
FIG. 2 is a cross sectional side view in more detail of a patient interface circuit for use with the continuous high-frequency oscillation breathing therapy apparatus of present invention.

FIG. 2 is a cross sectional side view in more detail of patient interface circuit comprising circuit tubes 10 and 25, breathing head assembly, mouthpiece 18, and nebulizer 21. Circuit tube 25 connects to the bottom of nebulizer 21, which, in turn, connects to aerosol entrainment port 20 located at the rearmost bottom portion of breathing head assembly 11. Circuit tube 10 connects to the rearmost end of breathing head assembly 11 by connecting directly to an injector nozzle 13 which is positioned in the rear portion of breathing head assembly 11.

In the rear portion of breathing head assembly 11, above injector nozzle 13 is at least one of aft apertures 14 which open the shell of breathing head assembly 11 to the ambient. Inside breathing head assembly 11 is mounted a venturi tube 17 which is anchored in the rear by the annular support of rear venturi support flange 30 and near the middle of breathing head 11 by two forward venturi support flanges 28 and 29 in such a manner that the shell of breathing head assembly 11 functions as a shroud for venture tube 17. Rear venturi support flange 30 contains several rear flange communication ports 16 which are longitudinal holes that perforate it circumferentially allowing communication between both sides of flange 30. Likewise, forward venturi support flanges 28 and 29 are perforated circumferentially and longitudinally by several forward flange communication ports 26 and 27 allowing communication between both sides of each of flanges 28 and 29. On top, near the middle of breathing head assembly 11 is at least one of forward apertures 15 which open the interior of breathing head assembly 11 shell to atmosphere. The forward portion of venturi tube 17 is sufficiently separated from the sides of breathing head assembly 11 shell so as to allow a circumferential communication space 12 which completes a communication corridor which extends from the rearmost cavity of breathing head assembly 11 through mouthpiece 18 and mouthpiece opening 19.

Figure 3:
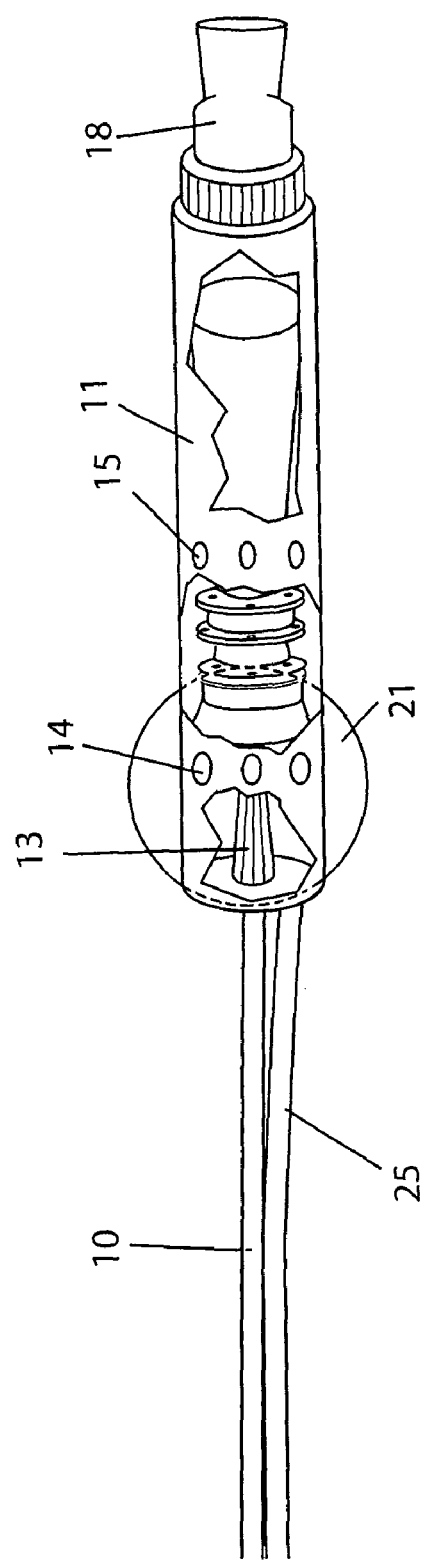
FIG. 3 is a cross sectional top view in more detail of a patient interface circuit for use with the continuous high-frequency oscillation breathing therapy apparatus of present invention.

FIG. 3 is a cross sectional top view in more detail of a patient interface circuit comprising circuit tubes 10 and 25, breathing head assembly 11, nebulizer 21, and mouthpiece 18. Circuit tube 25 connects to the bottom of nebulizer 21. Circuit tube 10 connects to the rearmost end of breathing head assembly 11 by connecting directly to injector nozzle 13 which is positioned in the rearmost portion of breathing head assembly 11. This top view shows placement of aft apertures 14 and forward apertures 15, which open shell of breathing head assembly 11 to the ambient.

Operation of the breathing treatment apparatus, pictured in FIGS. 1, 2, and 3, begins by loading a predetermined liquid medicament into nebulizer 21 by first detaching it from aerosol entrainment port 20. After filled nebulizer 21 is reattached, therapy is initiated by turning on source gas 1, which may be a compressor within the device, or an external pressurized gas source such as air or oxygen. Gas travels through source gas supply tube 2 into pressure reduction regulator 3 whereby it is modulated to a suitable constant flow. Reduction regulator 3 can be pre-set at the factory to a desirable flow in order to maximize the simplicity of the therapy. The regulated gas then flows through tube 4 to connector tee 5 which splits the gas into two streams. One goes into tube 22 where it is further regulated by reducing orifice 23, and then continues to circuit connector 24. Circuit connector 24 connects circuit tube 25 which carries gas to the bottom of nebulizer 21. Nebulizer 21 converts the liquid medication into aerosol which enters into aerosol entrainment port 20, ushering the aerosol into the rear cavity of breathing head assembly 11.

Meanwhile, the other stream of gas that was split at connector tee 5 continues into tube 6 and travels to flow interrupter valve 7. Valve 7 chops the constant gas flow into high-frequency pulses by interrupting it at regular intervals so that the flow becomes divided into substantially equal volumes, or pulses, at the rate of 1 to 15 hertz. Valve 7 can be pre-set at the factory to a predetermined rate to maximize the simplicity of the therapy. Because the flow is constant and the pulses are substantially equal, the resulting pulsatile pressure amplitude is substantially constant. That is to say that the difference between the lowest pressure and the highest pressure of each pulse is substantially equal.

The high-frequency flow then continues through circuit 8 to circuit connector 9. Circuit connector 9 connects circuit tube 10 which carries the gas to the rearmost portion of breathing head assembly 11. Here, the high-frequency pulses enter injector nozzle 13 which directs them into the rear opening of venturi tube 17.

The continuous high-frequency pulsatile flow enters into venturi tube 17 which may either amplify or attenuate it. As the flow enters venturi tube 17, given little or no resistance at mouthpiece opening 19, the flow is amplified. As the flow encounters the narrowing throat of venturi tube 17, its velocity increases. Additional gas then enters via aft aperture 14 by virtue of two processes. First, the increased velocity lowers surrounding pressures creating a vacuum effect, first described by Swiss mathematician Daniel Bernoulli in 1738, pulling in or entraining additional gas. Second, the friction between the high-speed molecules and the adjacent low-speed molecules has the effect of pulling the low-speed gas molecules into the stream of the high-speed gas.

In effect, ambient gas is pulled into the rear cavity of breathing head assembly 11 through aft aperture 14 and aerosol entrainment port 20. As the velocity of the gas increases, the volume of entrained gas increases, and, therefore, overall flow increases.

However, as resistance at mouthpiece opening 19 increases, the entrainment process is impeded and overall flow is attenuated. Velocity within the venturi decreases, and, in turn, entrainment and flow both decrease. Thus, the device allows the patient to exhale back into it, and the device is provided with a built-in safety mechanism. As the patient exhales or airway compliance decreases, resistance downstream from the venturi tube increases. The resulting decrease in delivered flow also decreases pressure, thereby protecting the airways and allowing the patient to exhale.

The mixture of high-frequency pulsatile flow from injection nozzle 13, aerosol from port 20, and ambient air from aft entrainment apertures 14 continue through the lumen of venturi tube 17, exiting its forward opening into mouthpiece 18 and out mouthpiece opening 19 to the patient. The patient seals his or her lips around mouthpiece 18 and inhales the aerosolized pulses of gas, taking them deep into the lungs. The patient then exhales back into mouthpiece opening 19 as the therapy continues. The combination of aft apertures 14, forward apertures 15, rear flange communication ports 16, and forward flange communication ports 26 and 27 allow both ingress and egress of flow, serving both inhalation and exhalation without the need for complex mechanisms to open and close valves during the therapy.

As the patient continues the high-frequency oscillation breathing therapy, several things begin to happen. The medicated aerosol and the oscillation of the air column in the conducting airways help reduce viscosity of the secretions. The bi-level flow created by high-frequency intermittent delivery of gas begins to create wind shear forces. A small pulse enters the airways, and then the flow momentarily stops. During this pause, the pressure in the upper airways drops to zero. Small volumes of gas that were previously delivered into the airways now begin to exit, momentarily unencumbered by the zero-pressure in the upper airways. As these exiting volumes of gas increase in velocity they continually push secretions from small distal airways to the larger openings in the upper airways where they can be more easily removed.

Throughout the high-frequency oscillation therapy session, the intermittent positive-pressure pulses continue constantly as the patient inhales and exhales through mouthpiece opening 19. The exhaled breath travels from mouthpiece opening 19 into circumferential communication space 12 and exits forward apertures 15. Aft apertures 14 and forward apertures 15 are calibrated with flow interrupter 7 so that the patient is able to exhale back into mouthpiece opening 19 even as the high-frequency positive gas flow continues. This calibration allows ample opportunity for exhaled breath to escape in order to prevent the successive stacking of inhaled breaths in the airways.

Figure 4:
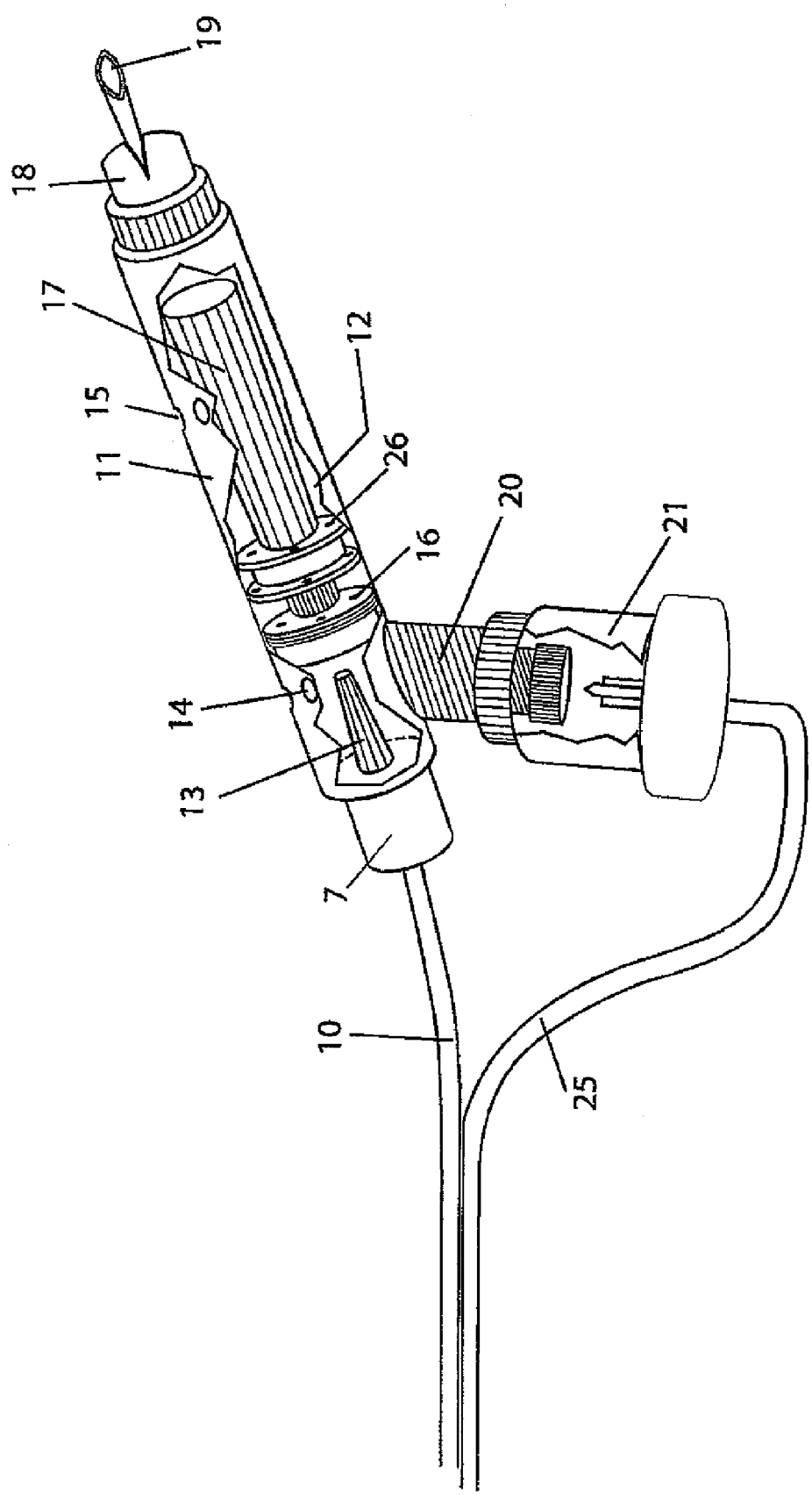
FIG. 4 is an alternate embodiment cross sectional side view of a patient interface circuit which includes within a means for interrupting positive gas flow for use with the breathing therapy apparatus of the present invention.

FIG. 4 depicts an alternate embodiment cross sectional side view of a patient interface circuit which includes within a means for interrupting positive gas flow for use with the continuous high-frequency oscillation breathing therapy apparatus of the present invention. Flow interrupter valve 7 is attached directly to the rearmost portion of breathing head assembly 11.

As regulated gas is directed through circuit tube 10 it enters into flow interrupter valve 7. Flow interrupter valve 7 chops the flow into high-frequency intermittent pulses which then go directly into injector nozzle 13 and continue the process as described above. This embodiment allows most of the elements of the apparatus to be included within the patient interface circuit itself.

Figure 5:
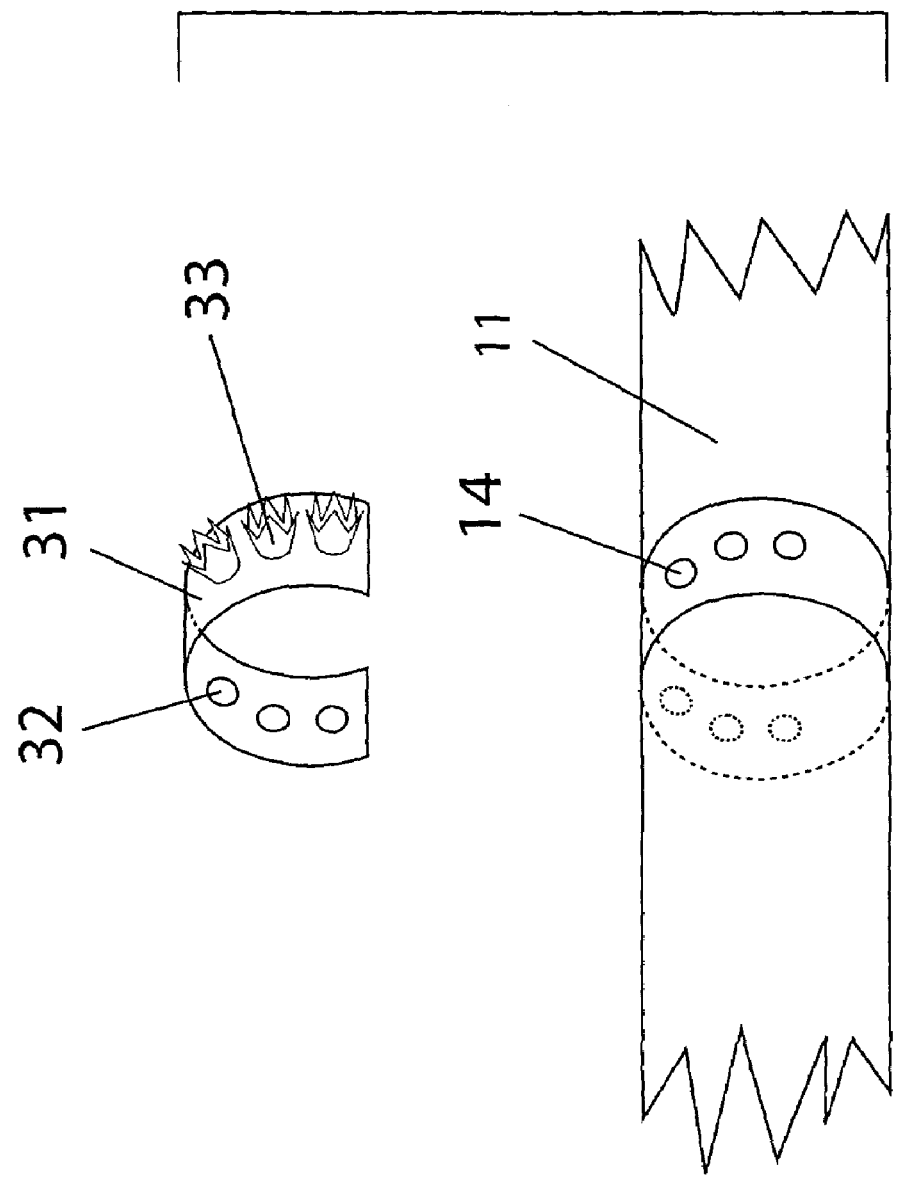
FIG. 5 is an alternate embodiment exploded sectional view of the aft apertures of the patient interface circuit with a means for their partial occlusion, and a means to prevent inadvertent complete occlusion of the apertures.

FIG. 5 presents an alternate embodiment exploded sectional view of aft apertures 14 of breathing head assembly 11 with an annular aperture adjustment collar 31 to provide a means for partially occluding apertures 14 in order to increase and decrease the ingress and egress of flow. Each of aperture adjustment collar holes 32 is surrounded by a safety crown 33 to prevent inadvertent complete occlusion.

Aperture adjustment collar 31 is slidably attached to breathing head assembly 11 adjacent to aft apertures 14 so that it can be axially adjusted. When aperture adjustment collar 31 is positioned so that aperture adjustment holes 32 align fully with aft apertures 14, maximum ingress and egress of flow is allowed. As aperture adjustment collar 31 is rotated so that aperture adjustment holes 32 begin to overlap aft apertures 14, effectively reducing the opening size of the apertures ingress and egress of flow becomes more diminished. The peaks of safety crown 33 eliminate inadvertent complete occlusion of aperture adjustment collar holes 32 by preventing a finger or hand from sealing them.

The embodiment depicted in FIG. 5 is applicable to aft apertures 14, which may be designated as primary for ingress of flow, and forward apertures 15 (FIGS. 1,2,3, &4), which may be designated as primary for egress of flow.

Figure 6:
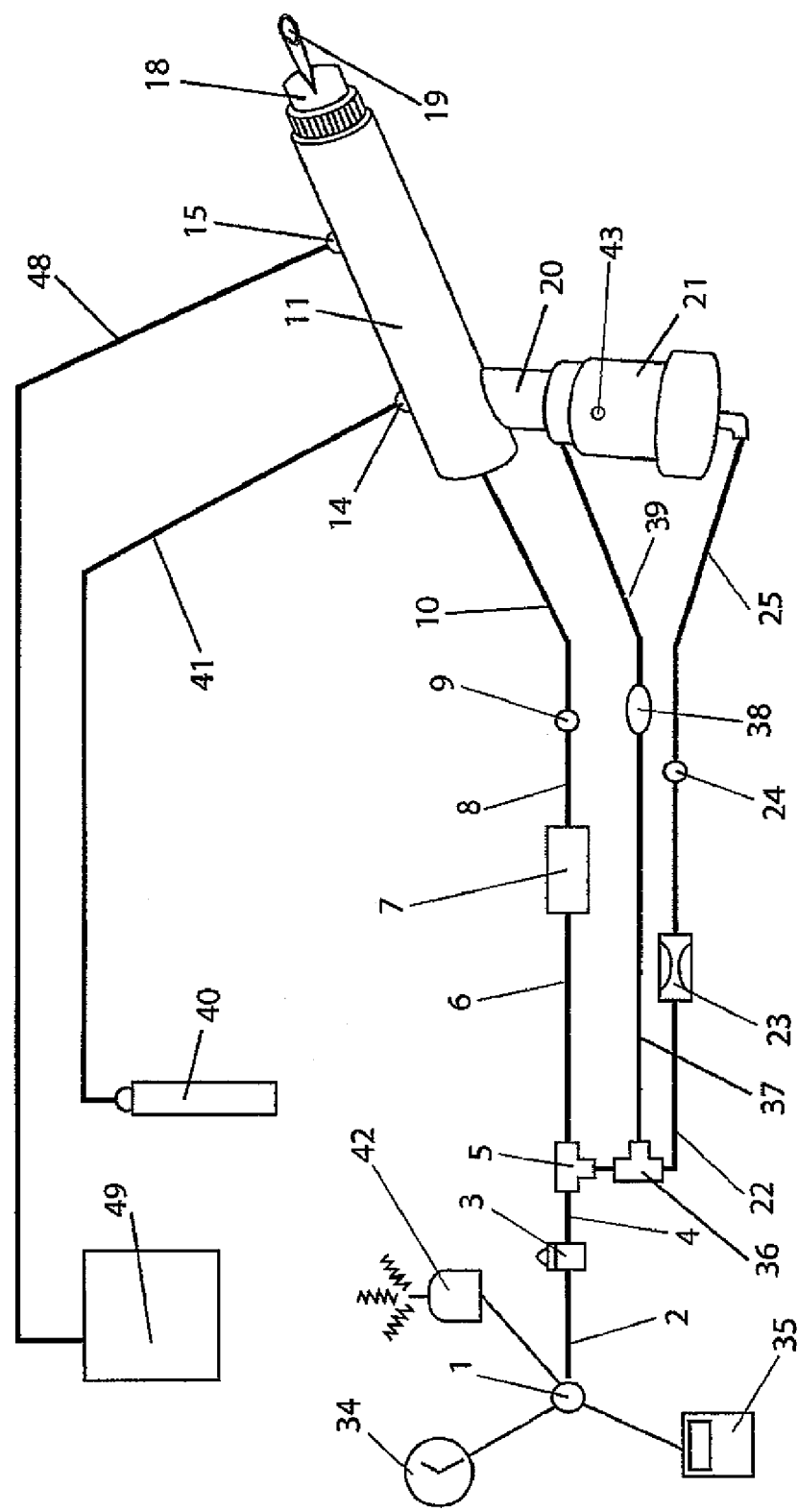
FIG. 6 is a schematic representation of an alternate embodiment of the continuous high-frequency oscillation breathing therapy apparatus of present invention.

FIG. 6 is a schematic diagram of an alternate embodiment that includes a number of additional features incorporated into the continuous high-frequency oscillation breathing treatment device. Timer 34 is connected to source gas 1, as is patient compliance monitor 35 and RFID transceiver 42. Reservoir tee 36 connects tube 37 to tube 22. Tube 37 connects by the other end to medicament reservoir 38. Medicament reservoir 38 is in communication with nebulizer 21 via tube 39. Specified gas source 40 connects to one end of inspiratory gas connector 41. The other end of inspiratory gas connector 41 connects to aft apertures 14. RFID tag 43 is embedded into a plastic wall of nebulizer 21. Evacuation reservoir 49 connects to forward apertures 15 by means of evacuation reservoir tube 48.

Timer 34 allows the clinician or the patient to pre-set a time for the treatment. At the end of the therapy session timer 34 can either turn off the apparatus by terminating source gas 1, or alarm to notify the patient that the treatment is over. Patient compliance monitor 35 logs use of the device in order to allow a clinician to determine whether or not the patient is utilizing the device. Medicament Reservoir 38 receives gas flow through tube 37, which is connected to tube 22 by reservoir tee 36. Medication is pumped from medicament reservoir 38 through tube 39 to nebulizer 21. This allows medication to be stored in a location remote from nebulizer 21, and medication can be continually pumped into nebulizer 21 as the therapy progresses.

Aft apertures 14 may be designated as primary for inspiration. In this case, the content of inspired gas can be controlled by connecting specified gas source 40 to aft apertures 14 by way of inspiratory gas connector 41. Forward apertures 15 may be designated as primary for exhalation. In this case, apertures 15 can be left open to the ambient or can be connected to evacuation reservoir 49. RFID (Radio Frequency Identification) transceiver 42, connected to source gas 1, can recognize identification information transmitted from RFID tag 43, embedded in nebulizer 21, to determine whether or not the component is compatible with the apparatus. RFID transceiver 42 can be programmed to prevent gas source 1 from being initiated if a component is incompatible.

Figure 7:
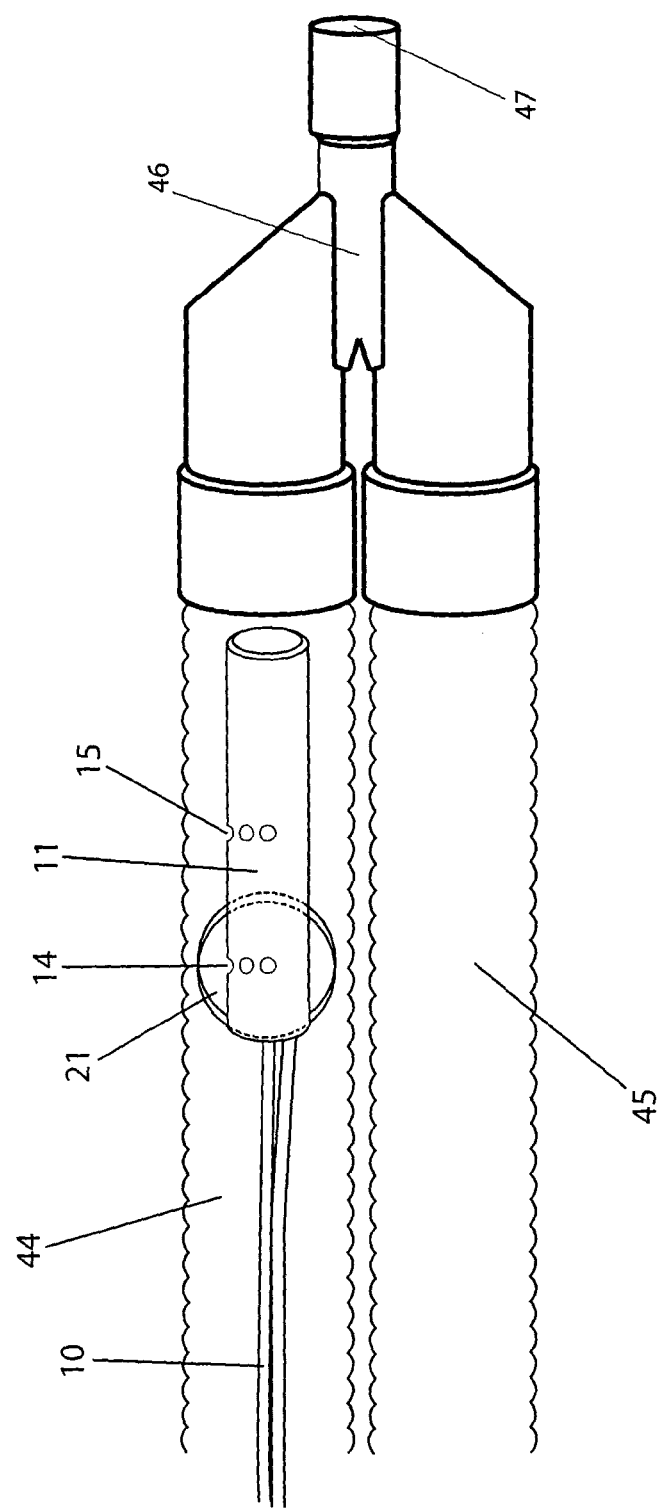
FIG. 7 is a top view of an alternate embodiment of the patient circuit of the continuous high-frequency oscillation breathing therapy apparatus of present invention is incorporated within a ventilator circuit.

FIG. 7 depicts a top-view perspective of an alternate embodiment of the continuous high-frequency oscillation apparatus that is incorporated into a ventilator breathing circuit. Ventilator circuit inspiratory limb 44 and ventilator circuit expiratory limb 45 are connected to ventilator circuit Y 46. Ventilator circuit Y 46 is in fluid communication with ventilator circuit Y patient connector 47. Mounted within ventilator circuit inspiratory limb 44 is breathing head assembly 11, which is connected to the continuous high-frequency oscillation apparatus by circuit tube 10, which is also mounted within ventilator circuit inspiratory limb 44.

The configuration presented in the alternate embodiment of FIG. 7 allows a treatment to be given to a patient connected to a ventilator without the need to disconnect the patient from the ventilator circuit.

What is claimed is:

1. A continuous high-frequency oscillation breathing treatment apparatus comprising:
   a source of gas under pressure;
   a reduction regulator for regulating the flow from gas source;
   means for interrupting continuous positive gas flow at a rate of at least 1 hertz and at most 15 hertz whereby the gas flow becomes pulsatile with a substantially constant pressure amplitude;
   a patient interface circuit that incorporates a fixed venturi tube, encased in a shroud with at least one aperture of predetermined size open to the ambient to allow ingress and egress of flow, and an aerosol entrainment port connectable to a nebulizer for entrainment of aerosol;
   said means for interrupting continuous gas flow in combination with said at least one aperture calibrated to allow exhalation and prevent stacking of successive volumes of gas in the airway of the patient.

2. The apparatus according to claim 1, wherein gas flow rate and pulsatile rate are settings, and wherein at least one of gas flow rate adjustment and pulsatile rate adjustment is pre-set at factory, whereby simplicity of use is maximized.

3. The apparatus according to claim 1, wherein at least one aperture can be partially occluded in order to increase and decrease the ingress and egress of flow.

4. The apparatus according to claim 1, further including a means to prevent inadvertent occlusion of said apertures.

5. The apparatus according to claim 1, further including a timing device that can at least automatically turn off said apparatus at end of therapy session or trigger an alarm to notify patient that treatment session is over.

6. The apparatus according to claim 1, further including a means for tracking use of said apparatus, whereby patient compliance with breathing therapy can be ascertained.

7. The apparatus according to claim 1, further including a medicament reservoir from which can be pumped medicament into a nebulizer connected to patient interface circuit.

8. The apparatus according to claim 1, wherein at least one aperture is designated as a primary for ingress of gas and is connected to a specified gas source in order to control the content of the gas being entrained, and at least one aperture is designated as primary for egress of gas and is connected to a reservoir that collects the evacuated gas and is open to the ambient.

9. The apparatus according to claim 1, wherein said patient interface circuit is, at least one of, connected to and incorporated within a ventilator circuit.

10. The apparatus according to claim 1, wherein said gas under pressure is supplied from an electronic compressor within the apparatus.

11. The apparatus according to claim 1, wherein at least two of said source of gas under pressure, said reduction regulator, said means for interrupting continuous positive gas flow, said patient interface circuit, and said means for interrupting continuous gas flow include an identification device to indicate their compatibility with one another.

12. The apparatus according to claim 11, wherein said identification device comprises at least one of a radio frequency identification (RFID) tag device and an RFID transceiver device.

13. The patient interface circuit for use with a continuous high-frequency oscillation breathing treatment apparatus comprising:
   means of connecting patient interface circuit to a continuous high-frequency oscillation breathing treatment apparatus;
   a fixed venturi tube, encased in a shroud with at least one aperture of predetermined size open to the ambient to allow ingress and egress of flow, and an aerosol entrainment port connectable to a nebulizer for entrainment of aerosol;
   said at least one aperture of patient interface circuit calibrated with continuous high-frequency oscillation breathing treatment apparatus to allow exhalation and prevent stacking of successive volumes of gas in the airway of the patient.

14. A continuous high-frequency oscillation breathing treatment apparatus comprising:
   a source of gas under pressure;
   a reduction regulator for regulating the flow from gas source;
   means for interrupting continuous positive gas flow at a predetermined, pre-set rate of at least 1 hertz and at most 15 hertz whereby the gas flow becomes pulsatile with a substantially constant pressure amplitude;
   a patient interface circuit that incorporates a venturi tube, encased in a shroud with at least one aperture of predetermined size open to the ambient to allow ingress and egress of flow, aerosol entrainment port connectable to a nebulizer for entrainment of aerosol;
   said means for interrupting gas flow in combination with said at least one aperture calibrated to allow exhalation and prevent stacking of successive volumes of gas in the airway of the patient.

15. The apparatus according to claim 14, wherein gas flow adjustment to said apparatus is pre-set at factory.

16. The apparatus according to claim 14, wherein at least one aperture can be partially occluded in order to increase and decrease the ingress and egress of flow.

17. The apparatus according to claim 14, further including a means to prevent inadvertent occlusion of said apertures.

18. The apparatus according to claim 14, further including a timing device that can at least automatically turn off said apparatus at end of therapy session or trigger an alarm to notify patient that treatment session is over.

19. The apparatus according to claim 14, further including a means for tracking use of said apparatus, whereby patient compliance with breathing therapy can be ascertained.

20. The apparatus according to claim 14, further including a medicament reservoir from which can be pumped medicament into a nebulizer connected to a patient interface circuit.

21. The apparatus according to claim 14, wherein at least one of said aperture is designated as primary for ingress of gas and is connected to a specified gas source in order to control the content of the gas being entrained, and at least one of said aperture is designated as primary for egress of gas and is at least one of connected to a reservoir that collects the evacuated gas and open to the ambient.

22. The apparatus according to claim 14, wherein said patient interface circuit is at least one of connected to and incorporated within a ventilator circuit.

23. The apparatus according to claim 14, wherein said gas under pressure is supplied from an electronic compressor within the apparatus.

24. The apparatus according to claim 14, wherein at least two of said source of gas under pressure, said reduction regulator, said means for interrupting continuous positive gas flow, said patient interface circuit and said means for interrupting gas flow include an identification device to indicate their compatibility with one another.

25. The apparatus according to claim 24, wherein said identification device comprises at least one of a radio frequency identification (RFID) tag device and an RFID transceiver device.

26. A continuous high-frequency oscillation breathing treatment apparatus comprising:
   a source of gas under pressure;
   a pre-set reduction regulator for regulating the flow from gas source;
   means for interrupting positive gas flow resulting in a predetermined, pre-set rate of at least 1 hertz and at most 15 hertz whereby the gas flow becomes pulsatile with a substantially constant pressure amplitude;
   a patient interface circuit that incorporates a venturi tube, encased in a shroud with at least one aperture of predetermined size open to the ambient to allow ingress and egress of flow, and an aerosol entrainment port connectable to a nebulizer for entrainment of aerosol;
   said means for interrupting continuous gas flow in combination with said at least one aperture calibrated to allow exhalation and prevent stacking of successive volumes of gas in the airway of the patient.

27. The apparatus according to claim 26, wherein at least one aperture can be partially occluded in order to increase and decrease the ingress and egress of flow.

28. The apparatus according to claim 26, further including a means to prevent inadvertent occlusion of said apertures.

29. The apparatus according to claim 26, further including a timing device that can at least automatically turn off said apparatus at end of therapy session or trigger an alarm to notify patient that treatment session is over.

30. The apparatus according to claim 26, further including a means for tracking use of said apparatus, whereby patient compliance with breathing therapy can be ascertained.

31. The apparatus according to claim 26, further including a medicament reservoir from which can be pumped medicament into a nebulizer connected to patient interface circuit.

32. The apparatus according to claim 26, wherein at least one of said aperture is designated as primary for ingress of gas and is connected to a specified gas source in order to control the content of the gas being entrained, and at least one of said aperture is designated as primary for egress of gas and is at least one of connected to a reservoir that collects the evacuated gas and open to the ambient.

33. The apparatus according to claim 26, wherein said patient interface circuit is at least one of connected to and incorporated within a ventilator circuit.

34. The apparatus according to claim 26, wherein said gas under pressure is supplied from an electronic compressor within the apparatus.

35. The apparatus according to claim 26, wherein at least two of said source of gas, said reduction regulator said means for interrupting positive gas flow, said patient interface circuit, and said means for interrupting continuous gas flow include an identification device to indicate their compatibility with one another.

36. The apparatus according to claim 35, wherein said identification device comprises at least one of a radio frequency identification (RFID) tag device and an RFID transceiver device.

37. A continuous high-frequency oscillation breathing treatment apparatus comprising:
  a source of gas under pressure;
  a reduction regulator for regulating the flow from gas source;
  a patient interface circuit that incorporates a means for interrupting positive gas flow at a rate of at least 1 hertz and at most 15 hertz whereby the gas flow becomes pulsatile with a substantially constant pressure amplitude, a fixed venturi tube, encased in a shroud with at least one aperture of predetermined size open to the ambient to allow ingress and egress of flow, an aerosol entrainment port connectable to a nebulizer for entrainment of aerosol, and said means for interrupting gas flow in combination with said at least one aperture calibrated to allow exhalation and prevent stacking of successive volumes of gas in the airway of the patient.

38. The apparatus according to claim 37, wherein gas flow rate and pulsatile rate are settings, and wherein at least one of gas flow rate and pulsatile rate adjustments to said apparatus is pre-set at factory, whereby simplicity of use is maximized.

39. The apparatus according to claim 37, wherein at least one aperture can be partially occluded in order to increase and decrease the ingress and egress of flow.

40. The apparatus according to claim 37, further including a means to prevent inadvertent occlusion of said apertures.

41. The apparatus according to claim 37, further including a timing device that can at least one of automatically turn off said apparatus at end of therapy session and alarm to notify patient that treatment session is over.

42. The apparatus according to claim 37, further including a means for tracking use of said apparatus, whereby patient compliance with breathing therapy can be ascertained.

43. The apparatus according to claim 37, further including a medicament reservoir from which can be pumped medicament into a nebulizer connected to patient interface circuit.

44. The apparatus according to claim 37, wherein at least one of said aperture is designated as primary for ingress of gas and is connected to a specified gas source in order to control the content of the gas being entrained, and at least one of said aperture is designated as primary for egress of gas and is at least one of connected to a reservoir that collects the evacuated gas and open to the ambient.

45. The apparatus according to claim 37, wherein said patient interface circuit is at least one of connected to and incorporated within a ventilator circuit.

46. The apparatus according to claim 37, wherein said gas under pressure is supplied from an electronic compressor within the apparatus.

47. The apparatus according to claim 37, wherein at least two of said source of gas under pressure, said reduction regulator, and said patient interface circuit include an identification device to indicate their compatibility with one another.

48. The apparatus according to claim 47, wherein said identification device comprises at least one of a radio frequency identification (RFID) tag device and an RFID transceiver device.

* * * * *

UNITED STATES PATENT AND TRADEMARK OFFICE
CERTIFICATE OF CORRECTION

| | |
|---|---|
| PATENT NO. | : 7,191,780 B2 |
| APPLICATION NO. | : 10/666428 |
| DATED | : March 20, 2007 |
| INVENTOR(S) | : Joseph Dee Faram |

It is certified that error appears in the above-identified patent and that said Letters Patent is hereby corrected as shown below:

In the Abstract, line 3, delete "clearings" and insert --clearing--.

In the Abstract, line 3, insert --from-- after "secretions".

Column 7, line 42, insert --,-- after "apertures".

Column 11, line 24, insert --,-- after "regulator".

Signed and Sealed this

First Day of May, 2007

JON W. DUDAS
*Director of the United States Patent and Trademark Office*